(12) United States Patent
Carlier et al.

(10) Patent No.: US 10,099,924 B2
(45) Date of Patent: Oct. 16, 2018

(54) PROCESS FOR MANUFACTURING A PURIFIED AQUEOUS HYDROGEN PEROXIDE SOLUTION

(71) Applicant: Solvay SA, Brussels (BE)

(72) Inventors: Juan-Teva Carlier, Tongrinne (BE); Pierre Dournel, Brussels (BE); Henk Venbrux, Tervuren (BE); Hooghe Lieven, Beveren-Waas (BE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 15/026,754

(22) PCT Filed: Oct. 2, 2014

(86) PCT No.: PCT/EP2014/071121
§ 371 (c)(1),
(2) Date: Apr. 1, 2016

(87) PCT Pub. No.: WO2015/049327
PCT Pub. Date: Apr. 9, 2015

(65) Prior Publication Data
US 2016/0251222 A1   Sep. 1, 2016

(30) Foreign Application Priority Data

Oct. 2, 2013  (EP) .................................... 13187128
Jul. 3, 2014  (EP) .................................... 14175503

(51) Int. Cl.
*C07D 301/12* (2006.01)
*C01B 15/013* (2006.01)
*C07D 303/04* (2006.01)

(52) U.S. Cl.
CPC .......... *C01B 15/013* (2013.01); *C07D 303/04* (2013.01)

(58) Field of Classification Search
CPC ............................ C07D 303/04; C01B 15/013
USPC ......................................................... 549/531
See application file for complete search history.

(56) References Cited

U.S. PATENT DOCUMENTS

| 5,232,680 | A | 8/1993 | Honig et al. |
| 5,302,367 | A | 4/1994 | Signorini et al. |
| 5,614,165 | A | 3/1997 | Sugihara et al. |
| 6,224,845 | B1* | 5/2001 | Pennetreau ........... C01B 15/013 423/272 |
| 8,558,020 | B2* | 10/2013 | Liebens ................. C01B 15/01 423/415.1 |

(Continued)

FOREIGN PATENT DOCUMENTS

| CN | 1616345 A | 5/2005 |
| CN | 101223152 A | 7/2008 |

(Continued)

OTHER PUBLICATIONS

Hawley, The Condensed Chemical Dictionary, 1971, p. 455-456, 4 pages in total.*

(Continued)

*Primary Examiner* — Taylor V Oh
(74) *Attorney, Agent, or Firm* — Osha Liang LLP

(57) ABSTRACT

Process for manufacturing a purified aqueous hydrogen peroxide solution, in which a crude aqueous hydrogen peroxide solution is subjected to a washing operation with at least one organic solvent, and wherein an organophosphorus chelating agent is added to the organic solvent.

14 Claims, 4 Drawing Sheets

(56) References Cited

U.S. PATENT DOCUMENTS

| | | |
|---|---|---|
| 2006/0009371 A1 | 1/2006 | Wang et al. |
| 2008/0167484 A1 | 7/2008 | Schindler et al. |
| 2011/0130579 A1 | 6/2011 | Muller et al. |
| 2013/0157134 A1 | 6/2013 | Kintaka |

FOREIGN PATENT DOCUMENTS

| | | | |
|---|---|---|---|
| EP | 0529723 A1 | | 3/1993 |
| EP | 0965562 A1 | | 12/1999 |
| EP | 1167290 A2 | | 1/2002 |
| JP | 11139811 | * | 5/1999 |
| WO | 2005/063620 A2 | | 7/2005 |
| WO | 2010109011 A1 | | 9/2010 |
| WO | 2012/076543 A1 | | 6/2012 |
| WO | 2013/018758 A1 | | 2/2013 |

OTHER PUBLICATIONS

Georgopoulou, Z. J., et al—"Feasibility and cost of creating an iron-phosphate coating on pyrrhotite to prevent oxidation", 1996, Environmental Geology (Berlin), vol. 28, Issue No. 2, pp. 61-69; 9 pgs.

Evangelou, V. P.—"Pyrite microencapsulation technologies: Principles and potential field application", 2001, Ecological Engineering, vol. 17, Issue No. 2-3, Elsevier Science B.V., pp. 165-178; 14 pgs.

Scaccia, S., et al—"Thermoanalytical investigation of iron phosphate obtained by spontaneous precipitation from aqueous solutions", 2002, Thermochimica Acta, vol. 383, Issue No. (1-2), Elsevier Science B.V., pp. 145-152; 8 pgs.

Scaccia, S., et al—"Thermoanalytical study of iron(III) phosphate obtained by homogeneous precipitation from different media", 2004, Thermochimica Acta, vol. 413, Issue No. (1-2), Elsevier Science B.V., pp. 81-86; 6 pgs.

Gajda, B., et al—"The effect of tributyl phosphate on the extraction of nickel(II) and cobalt(II) ions with di(2-ethylhexyl)phosphoric acid", 2007, Physiochemical Problems of Mineral Processing, vol. 41, pp. 145-152; 9 pgs.

Pa Ho Hsu, "Comparison of iron(III) and aluminum in precipitation of phosphate from solution", 1976, Water Research, vol. 10, Pergamon Press pp. 903-907; 5 pgs.

"Hydrogen Peroxide", Gustaff Goor et al., Ullman's Encyclopedia of Industrial Chemistry, vol. 18, pp. 393-427, 2012, http://onlinelibrary.wiley.com/doi/10.1002/14356007.a13_443.pub2/pdf.

"Solvay's position and strategy in hydrogen peroxide"; London Investors Morning, Sep. 30, 2010; http://www.solvay.com/en/binaries/20100930_LondonMorning-35304.pdf (27 pages).

Notification of Third Office Action dated May 17, 2018, by the State Intellectual Property Office of the Peoples Republic of China in corresponding Chinese Patent Application No. CN-2014800546343, with English translation (7 pages).

* cited by examiner

PROCESS FOR MANUFACTURING A PURIFIED AQUEOUS HYDROGEN PEROXIDE SOLUTION This application is a U.S. national stage entry under 35 U.S.C. § 371 of International Application No. PCT/EP2014/071121, filed Oct. 2, 2014, which claims priority to European patent application No. 13187128.7, filed on Oct. 2, 2013 and European patent application No. 14175503.3, filed on Jul. 3, 2014, the whole content of each of these applications is hereby incorporated herein by reference for all purposes.

The present invention relates to a process for manufacturing a purified aqueous hydrogen peroxide solution.

Hydrogen peroxide is one of the most important inorganic chemicals to be produced worldwide. Its industrial applications include textile, pulp and paper bleaching, organic synthesis (propylene oxide), the manufacture of inorganic chemicals and detergents, environmental and other applications.

Synthesis of hydrogen peroxide is predominantly achieved by using the Riedl-Pfleiderer process, also called anthraquinone loop process or AO (auto-oxidation) process.

This well known cyclic process makes use typically of the auto-oxidation of at least one alkylanthrahydroquinone and/or of at least one tetrahydroalkylanthrahydroquinone, most often 2-alkylanthraquinone, to the corresponding alkylanthraquinone and/or tetrahydroalkylanthraquinone, which results in the production of hydrogen peroxide.

The first step of the AO process is the reduction in an organic solvent of the chosen quinone (alkylanthraquinone or tetrahydroalkylanthraquinone) into the corresponding hydroquinone (alkylanthrahydroquinone or tetrahydroalkylanthrahydroquinone) using hydrogen gas and a catalyst. The mixture of organic solvents, hydroquinone and quinone species (working solution, WS) is then separated from the catalyst and the hydroquinone is oxidized using oxygen, air or oxygen-enriched air thus regenerating the quinone with simultaneous formation of hydrogen peroxide. The organic solvent of choice is typically a mixture of two types of solvents, one being a good solvent of the quinone derivative (for instance a mixture of aromatic compounds) and the other being a good solvent of the hydroquinone derivative (for instance a long chain alcohol). Hydrogen peroxide is then typically extracted with water and recovered in the form of a crude aqueous hydrogen peroxide solution, and the quinone is returned to the hydrogenator to complete the loop.

It is known to use hydrogen peroxide in the presence of a heterogeneous catalyst to convert an olefin into an oxirane, more particularly to convert propylene into propylene oxide (1,2-epoxypropane) by reaction with hydrogen peroxide. Such a process is generally performed in huge plants which consume huge amounts of hydrogen peroxide. Like many other (catalytic) organic oxidation processes, it requires pure reagents with no risk of process precipitation, i.e. a metal content of the order of 10 ppb. In the case of propylene oxide manufacture, it has namely been observed that if metals are present, like Fe (coming from the material of construction of the apparatus used) or Al (coming from the catalyst) and even in low amounts of between 50 and 200 ppb, these react with the reactives fed to the reactor and lead to the precipitation of insolubles which in turn leads to filter clogging.

Patent applications EP 529723 and EP 965562 in the name of the Applicant describe a process for manufacturing a purified aqueous hydrogen peroxide solution, in which a crude aqueous hydrogen peroxide solution is subjected to a washing operation with at least one organic solvent. In such a process, washing is intended to remove from the peroxide, working solution residuals, i.e. quinones and their degradation products. The solvents are generally those of the AO process in question used normally for dissolving the quinones in order to make working solution (the solvents being generally circulated from crude washing to main loop). The purpose of this traditional crude washing is to reduce TOC (organic matter) in the peroxide, and it has no effect on inorganic impurities (Al, Fe etc.).

On the other hand, various techniques (membrane filtration, distillation etc) are available when ultrapure peroxides are needed, but they are either too costly or not suitable for high volume (>100000 t per year) applications.

The purpose of the present invention is hence to provide an improved process for the preparation of hydrogen peroxide, in particular a new method for producing hydrogen peroxide with a low concentration of easily precipitating metals (Al, Fe, Cr . . . ) which is not expensive and is suitable for high volumes.

The present invention therefore concerns a process for manufacturing a purified aqueous hydrogen peroxide solution, in which a crude aqueous hydrogen peroxide solution is subjected to a washing operation with at least one organic solvent, and wherein an organophosphorus chelating agent is added to the organic solvent.

The term "washing" is intended to denote any treatment, which is well known in the chemical industry, of a crude aqueous hydrogen peroxide solution with an organic solvent which is intended to reduce the content of impurities in the aqueous hydrogen peroxide solution. This washing can consist, for example, in extracting impurities in the crude aqueous hydrogen peroxide solution by means of an organic solvent in apparatuses such as centrifugal extractors or liquid/liquid extraction columns, for example, operating counter-currentwise. Liquid/liquid extraction columns are preferred. Among the liquid/liquid extraction columns, columns with perforated plates are preferred.

In a preferred embodiment, the crude aqueous hydrogen peroxide solution is washed several times i.e. at least two times consecutively or even more times as required to reduce the content of impurities at a desired level.

The expression "crude aqueous hydrogen peroxide solution" is intended to denote the solutions obtained directly from a hydrogen peroxide synthesis step or from a hydrogen peroxide extraction step or from a storage unit. The crude aqueous hydrogen peroxide solution can have undergone one or more treatments to separate out impurities prior to the washing operation according to the process of the invention. It typically has an H2O2 concentration within the range 30-45% by weight.

It is preferred to bring the organic solvent in counter-current relative to the crude aqueous hydrogen peroxide solution. The efficacy of the washing depends on the flow rate of the organic solvent. The efficacy of the washing is improved when the flow rate of the organic solvent is increased. The volume of organic solvent used for the washing is defined as the quotient of the flow rate of solvent and of the flow rate of the hydrogen peroxide solution. The volume used in the process according to the invention is generally at least 3 l per $m^3$ of crude aqueous hydrogen peroxide solution. Preferably, the volume is at least 25 l per $m^3$ of aqueous hydrogen peroxide solution. The volume is generally not more than 100 l per $m^3$ of aqueous hydrogen peroxide solution. The volume is preferably not more than 75 l per $m^3$ of aqueous hydrogen peroxide solution. The washing temperature is generally at least 10° C. It is preferred to work at a temperature of at least 40° C. Generally, the temperature is not more than 65° C., preferably not more than 60° C. The washing time depends on the size of the apparatus chosen and on the flow rate of crude aqueous hydrogen peroxide solution introduced into the apparatus.

The metals which are removed by the process are those which easily precipitate in contact with phosphates like Al, Fe and Cr. Good results are obtained for Al and/or Fe removal. Hence, "purified" means with reduced metal content, more particularly reduced Al and/or Fe content, preferably of less than 100 ppb of Al and/or Fe (typically in the range of the $10^{th}$ of ppb, preferably in the range of the ppb, even more preferably below the ppb). In preferred embodiments, the Cr content can also be reduced to the same level (i.e. less than 100 ppb, typically in the range of the $10^{th}$ of ppb, in the range of the ppb or even below).

The organophosphorous chelating agent according to the invention is an organic molecule able of forming complexes with metals and in particular, with the above mentioned metals (Al and/or Fe and optionally Cr). It preferably comprises an acid group, preferably a phosphonic acid group. It is also preferably void of S (sulfur) in order namely not to influence negatively the hydrogen peroxide stability. Chelating agents which give good results are DEHPA (di-(2-ethylhexyl) phosphoric acid) and Cyanex® 272 (bis(2,4,4-trimethylpentyl)phosphinic acid). The former is preferred.

Preferably, the process of the invention comprises the following steps:
a) hydrogenation, in the presence of a catalyst, of a working solution comprising at least one organic solvent and at least one alkylanthraquinone to obtain the corresponding alkylanthrahydroquinone,
b) separation of the hydrogenated working solution comprising the alkylanthrahydroquinone from the catalyst,
c) oxidation of the recovered hydrogenated working solution from step b) to form hydrogen peroxide,
d) separation, from the working solution, of said hydrogen peroxide during and/or subsequently to said oxidation step, preferably with an aqueous medium, and
e) recycling of the recovered working solution to step a)
and the crude aqueous hydrogen peroxide solution separated in step d) is subjected to the washing operation.

The term "alkylanthraquinones" is intended to denote 9,10-anthraquinones substituted in position 1, 2 or 3 with at least one alkyl side chain of linear or branched aliphatic type comprising at least one carbon atom. Usually, these alkyl chains comprise less than 9 carbon atoms and, preferably, less than 6 carbon atoms. Examples of such alkylanthraquinones are 2-ethylanthraquinone, 2-isopropylanthraquinone, 2-sec- and 2-tert-butylanthraquinone, 1,3-, 2,3-, 1,4- and 2,7-dimethylanthraquinone, 2-iso- and 2-tert-amylanthraquinone and mixtures of these quinones.

The term "alkylanthrahydroquinones" is intended to denote the 9,10-hydroquinones corresponding to the 9,10-alkylanthraquinones specified above.

In this embodiment of the invention, the alkylanthraquinones can be dissolved in various types of solvents, especially in the solvents typically used in the working solution of the well known AO process. For instance, the alkylanthraquinones can be dissolved in a single solvent or in a mixed solvent comprising at least one aromatic solvent and at least one aliphatic or alicyclic alcohol, particularly in a mixed solvent. Aromatic solvents are for instance selected from benzene, toluene, xylene, tert-butylbenzene, trimethylbenzene, tetramethylbenzene, naphthalene, methylnaphthalene mixtures of polyalkylated benzenes, and mixtures thereof. Aliphatic or alicyclic alcohols are for example selected from amyl alcohol, nonyl alcohol, isoheptyl alcohol, diisobutylcarbinol, methylcyclohexanol, and mixtures thereof. Useful single solvents are, among others, a ketone, an ester, an ether, or mixtures thereof. Often used solvents are S-150 and/or diisobutylcarbinol (DiBC), preferably a mixture of both. S-150 means a commercially available aromatic hydrocarbon solvent of type 150 from the Solvesso® series. S-150 (Solvesso®-150; CAS no. 64742-94-5) is known as an aromatic solvent of high aromatics which offer high solvency and controlled evaporation characteristics that make them excellent for use in many industrial applications and in particular as process fluids. The Solvesso® aromatic hydrocarbons are available in three boiling ranges with varying volatility, e.g. with a distillation range of 165-181° C., of 182-207° C. or 232-295° C. They may be obtained also naphthalene reduced or as ultra-low naphthalene grades. Solvesso® 150 (S-150) is characterized as follows: distillation range of 182-207 C; flash point of 64° C.; aromatic content of greater than 99% by wt; aniline point of 15° C.; density of 0.900 at 15° C.; and an evaporation rate (nButAc=100) of 5.3.

In a first sub-embodiment of the invention, the organic solvent used for the washing operation is a part of the working solution used in the alkylanthraquinone process.

This sub-embodiment makes it possible to modify the feed flow rate of organic solvent in the operation for washing the crude aqueous hydrogen peroxide solution obtained according to the alkylanthraquinone process. It is in fact desirable to provide a flow rate of organic solvent which is sufficient to feed the operation for washing an aqueous hydrogen peroxide solution. It is particularly desirable to be able to adjust the flow rate of organic solvent as a function of the desired washing efficacy and as a function of the amount of crude aqueous hydrogen peroxide solution to be subjected to the washing operation.

In the alkylanthraquinone process, the working solution is available in an amount which is large enough to make it possible to take an amount of organic solvent which is required to reach the desired feed flow rate of organic solvent.

The process according to this sub-embodiment of the invention has economic and technical advantages since it avoids the use of large amounts of fresh organic solvent to feed the washing step. Fresh organic solvents are more expensive than purified solvents. Large amounts are difficult to generate since it is necessary to ensure a continuous feed of fresh organic solvent and its destruction after the washing operation.

In this sub-embodiment of the invention, the organic solvent, after washing, can be subjected to a regeneration treatment. It can then be recycled into the washing step. If necessary, it can be recycled into the working solution used in the alkylanthraquinone process.

In a second sub-embodiment of the invention, the organic solvent used for the washing operation is a dedicated solvent, not part of the working solution. This sub-embodiment has the advantage that the nature of the solvent can be chosen so that it shows a synergistic effect (metal extraction) with the organophosphorus chelating agent (in other words: it improves the metal extraction by the organophosphorus chelating agent). In that regard, solvents comprising other organophosphorus compounds (i.e. at least an organophosphorus compound different from the organophosphorus chelating agent) like alkyl-phosphates or alkyl-phosphonates are preferably used as solvents. Especially when the organophosphorus chelating agent is di-(2-ethylhexyl)phosphoric acid (DEHPA or HDEHP), good results are obtained with solvents comprising TOP (trioctylphosphate) or TEHP (triethylhexylphosphate). Solvents comprising dibutyl phosphoric acid (DBPA), tributyl phosphate (TBP) or Cyanex® 923 (trialkylphosphine oxides) can also be used.

In this sub-embodiment, the dedicated solvent is not recycled/recirculated in the main loop (of peroxide production) but instead, is regenerated and recycled in the washing step or disposed in order to avoid soluble metal accumulation in the process.

The regeneration treatments mentioned above consist, for example, in subjecting the solvent to one or more extractions, and to one or more treatments with a chemical reagent which is compatible with the organic solvent, in order to remove the impurities. The solvent regeneration is preferably done using an aqueous acidic solution for instance an aqueous nitric acid solution (HNO3). This solvent regeneration is in fact also an extraction, the acid transforming the organic metal complexes in inorganic salts (nitrates in the case of nitric acid) of said metals which are water soluble and hence are extracted from the solvent (organic phase) in an aqueous phase namely consisting of water in which the metal salts are dissolved. Hence, this regeneration can be done using classical industrial extraction equipment like a column, a centrifugal decanter etc.

Besides the nature of the chelating agent and of the solvent, several other parameters may be adapted in order to optimize the process of the invention, namely: the pH, the amount of chelating agent, the ratio peroxide to solvent and the temperature. Preferably, the pH is acidic because this limits hydrogen peroxide decomposition and also, the solubility of the chelating agent in said hydrogen peroxide.

FIG. 4 attached shows a bloc diagram of a preferred embodiment of the invention, according to which a crude hydrogen peroxide aqueous solution (1) is submitted to a washing operation (first extraction step 2) with an organic solvent to which an organophosphorus chelating agent has been added, and which actually is a mixture of fresh extraction solvent (3) and of regenerated solvent (8). This washing operation is in fact an extraction, the organic phase (solvent+chelating agent) being first mixed with the crude hydrogen peroxide solution in order to be able of forming complexes with the metals it contains and thereafter, two phases are separated to provide respectively a purified aqueous hydrogen peroxide solution (4) and an organic phase charged with metal complexes (5). The latter is then at least partly regenerated in a second extraction step (6) using an aqueous HNO3 solution (7) as explained above. At the issue of this regeneration step (6), there is provided an aqueous phase comprising metal nitrates (9) and a purified extraction solvent of which part (8) is recycled to the first extraction step (washing operation 2) and part (10) is removed to balance the process.

The present invention also relates to a process for manufacturing propylene oxide (1,2-epoxypropane) by reaction of propylene with hydrogen peroxide, said process using a hydrogen peroxide purified with a process as described above.

More generally, the present invention also relates to the use of a purified H2O2 solution for manufacturing propylene oxide, wherein "purified" is as defined above i.e. having an Al and/or Fe (and optionally also a Cr content) of less than 100 ppb, typically in the range of the 10th of ppb, preferably in the range of the ppb, even more preferably below the ppb of these elements.

Should the disclosure of any patents, patent applications, and publications which are incorporated herein by reference conflict with the description of the present application to the extent that it may render a term unclear, the present description shall take precedence.

The present invention is illustrated in a non limitative way by the Examples below and FIGS. 1 to 3 attached which relate to preferred embodiments thereof.

EXAMPLES 1 TO 4

Figure 1:
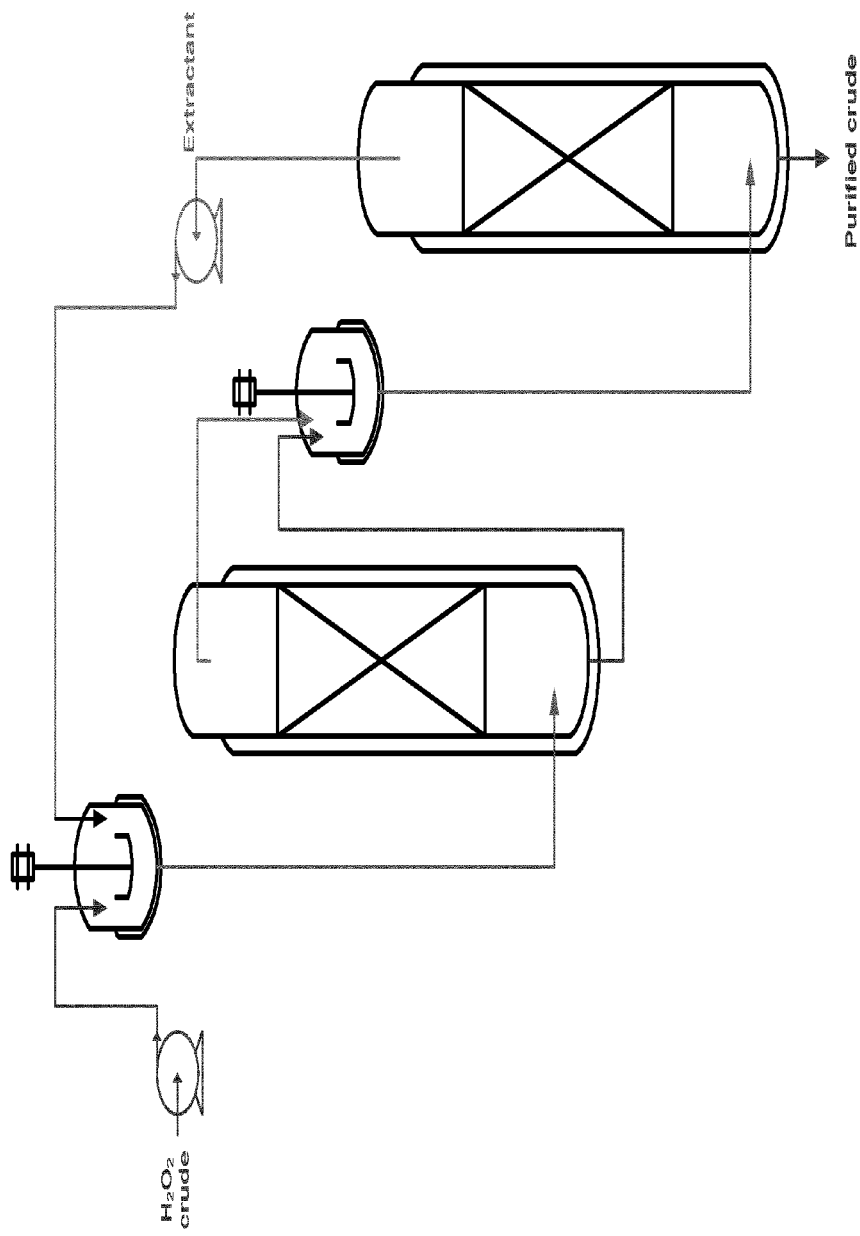
FIG. 1 is schematic diagram of the apparatus (installation) used for the continuous trial of Example 7.

DEHPA has been tested as a chelant to remove Al and Fe from a crude H2O2 solution having a peroxide concentration of 40% and the following metal content:
Al=220 ppb
Fe=110 ppb

Example 1: pH Optimization

A sample of hydrogen peroxide at 40% concentration is treated either with a nitric acid solution or with sodium hydroxide solution to obtain the desired pH. Then the hydrogen peroxide is mixed with the organic solution containing the solvent and the chelating agent in a plastic decanting funnel. The funnel was then shaken during 30 min and let to decant until a good separation is obtained between the organic and the aqueous phases. The treated hydrogen peroxide was recovered and analyzed for metal concentration by ICP. The ratio peroxide on organic phase (TOP+DEHPA) was set equal to 5.0. The amount of DEHPA in TOP was set equal to 2% by weight.

The results obtained are shown in table 1 below.

TABLE 1

| pH | Al in H2O2 crude ppb | Fe in H2O2 crude ppb | P in H2O2 crude ppm | Al removed (%) | Fe removed (%) |
|---|---|---|---|---|---|
|  | 180 | 24 | 8.3 | 5 | 76 |
| 2.0 | 170 | 17 | 12 | 26 | 85 |
| 2.5 | 150 | 14 | 20 | 35 | 87 |
| 3.0 | 140 | 26 | 36 | 36 | 76 |
| 1.5 | 150 | 54 | 77 | 35 | 55 |
| 4.0 | 180 | 74 | 81 | 22 | 33 |
| 4.5 | 180 | 80 | 83 | 22 | 27 |

These tests show that:
- the optimum pH range for Al and Fe removal is between 2.0 and 2.5 which is close to the natural pH of crude peroxide
- when the pH increases (especially above 3.5), the chelant (complexing agent) has a tendency to dissolve in the hydrogen peroxide as can be seen by the evolution of the P content.

Example 2: Optimization of the Ratio Peroxide/Organic and Amount of DEHPA

The same conditions as in Example 1 were used except that the pH was not adjusted before the test.

The results obtained are shown in table 2 below.

TABLE 2

| pH of H2O2 | H2O2/TOP ratio | DEHPA in TOP (%) | Al in H2O2 crude ppb | Fe in H2O2 crude ppb | P in H2O2 crude ppm | Al removed (%) | Fe removed (%) |
|---|---|---|---|---|---|---|---|
| 2 | 1 | 0 | 220 | 46 | 11 | 4 | 58 |
| 2 | 1 | 2 | 120 | 5 | 15 | 48 | 95 |
| 2 | 1 | 5 | 41 | <5 | 25 | 82 | >95 |
| 2 | 5 | 0 | 200 | 43 | 10 | 13 | 61 |
| 2 | 5 | 2 | 170 | 17 | 12 | 26 | 85 |
| 2 | 5 | 5 | 66 | <5 | 16 | 71 | >95 |
| 2 | 10 | 0 | 200 | 42 | 10 | 13 | 62 |
| 2 | 10 | 2 | 180 | 18 | 12 | 22 | 84 |
| 2 | 10 | 5 | 120 | <5 | 12 | 48 | >95 |

These tests show that the optimum metal removal is obtained with a low ratio peroxide to organic phase (1 to 1) and with a concentration of DEHPA of 5% by weight in TOP.

Example 3: Influence of Solvent: Solvesso®/DiBC Compared to TOP

As the solvent combination Solvesso®150/DiBC is often used on crude $H_2O_2$ production sites, it was interesting to check the efficiency of DEHPA in this type of solvent.

The tests performed at lab scale (again using the same procedure as in the previous examples) are shown in Table 3 below.

TABLE 3

| pH of H2O2 | H2O2/solvent ratio | DEHPA in S150/DBC (%) | Al in H2O2 crude ppb | Fe in H2O2 crude ppb | P in H2O2 crude ppm | Al removed (%) | Fe removed (%) |
|---|---|---|---|---|---|---|---|
| 2 | 1 | 1 | 180 | 47 | 11 | 22 | 57 |
| 3 | 1 | 1 | 190 | 50 | 14 | 17 | 55 |
| 4 | 1 | 1 | 190 | 33 | 15 | 17 | 70 |
| 5 | 1 | 1 | 220 | 13 | 27 | 4 | 88 |
| 6 | 1 | 1 | 12 | 12 | 80 | 95 | 89 |

These results indicate two main different trends in comparison with TOP
the optimum pH is much higher (close to 6.0) and might lead to a stability issue for hydrogen peroxide
the amount of DEHPA required for an optimum removal is lower than the one required for TOP systems (1% instead of 5%).

Example 4: Influence of Complexing Agents: CYANEX® 272 Compared to DEHPA

CYANEX® 272, a phosphonated component with a different structure than DEHPA and having the chemical formula is bis(2,4,4-trimethylpentyl)phosphinic acid (CAS: 83411-71-6) was used again in the same experimental conditions. The comparative tests performed at lab scale are shown in Table 4 below.

TABLE 4

| H2O2/TOP ratio | CYANEX in TOP (%) | Al in H2O2 CRUDE ppb | Fe in H2O2 CRUDE ppb | P in H2O2 crude ppm | Al removed (%) | Fe removed (%) |
|---|---|---|---|---|---|---|
| 1 | 0 | 220 | 46 | 11 | 4 | 58 |
| 1 | 2 | 160 | 6 | 15 | 30 | 95 |
| 1 | 5 | 160 | 6 | 18 | 30 | >95 |
| 5 | 0 | 200 | 43 | 10 | 13 | 61 |
| 5 | 2 | 170 | 12 | 12 | 26 | 89 |
| 5 | 5 | 160 | 5 | 14 | 30 | >95 |
| 10 | 0 | 200 | 42 | 10 | 13 | 62 |
| 10 | 2 | 170 | 19 | 11 | 26 | 83 |
| 10 | 5 | 160 | 9 | 13 | 30 | >95 |

These tests show that when using the best conditions optimized for DEHPA (pH=2, Ratio=1 and DEHPA=5%), the Al removal by CYANEX® is limited to 30% instead of 82% for DEHPA.

CYANEX® 272 has however a high efficiency for Fe removal (>95%) and similar to the one obtained with DEHPA.

Examples 5, 6 and 7

A multi-extraction process has been tested to remove Al, Fe and Cr from a crude $H_2O_2$ solution having a peroxide concentration of 40% and the following metal content:
Al=76 ppb
Fe=92 ppb
Cr=23 ppb Example 5: Test at Ambient Temperature A crude solution of hydrogen peroxide at 40% concentration was mixed with an organic solution containing a mixture of solvents and a chelating agent in a plastic decanting funnel. The organic solution consisted of:
80% w/w of Solvess®150
10% w/w of TOP
10% w/w of DEHPA The funnel was then shaken during 60 min at ambient temperature and let to decant for 24 hours. The treated hydrogen peroxide was separated from the organic phase, filtered on paper filters (597½ followed by 595) and a sample was taken for analysis.

The same sample of hydrogen peroxide was treated 5 times successively with a fresh aliquot of the organic chelating solution. At each step of the process, a sample was taken and analysed for metal concentration by ICP-MS.

The ratio peroxide on organic phase (S150+TOP+DEHPA) was the same at each step and equal to 10.

The results obtained are shown in Table 5 below:

TABLE 5

| | ICP analysis | | | Yield of removal | | |
|---|---|---|---|---|---|---|
| | Al µg/kg | Fe µg/kg | Cr µg/kg | Al % | Fe % | Cr % |
| Initial H2O2 | 76 | 92 | 23 | | | |
| extraction 1 | 5 | 0.29 | 16 | 93.4 | 99.7 | 30.4 |
| extraction 2 | 2 | 0.07 | 11 | 97.4 | 99.9 | 52.2 |
| extraction 3 | 1.5 | 0.09 | 8 | 98.0 | 99.9 | 65.2 |
| extraction 4 | 1.5 | 0.15 | 5 | 98.0 | 99.8 | 78.3 |
| extraction 5 | 1.4 | 0.08 | 3.1 | 98.2 | 99.9 | 86.5 |

These results show that:
The extracting process is efficient for Al, Fe and Cr at the natural pH of crude hydrogen peroxide The efficiency of the extracting process goes in the order: Fe>Al>Cr Example 6: Test at 50° C.

The same procedure as in Example 5 was repeated except that the temperature was set at 50° C. instead of ambient. The results obtained are shown in Table 6 below:

TABLE 6

|  | ICP analysis | | | Yield of removal | | |
| --- | --- | --- | --- | --- | --- | --- |
|  | Al µg/kg | Fe µg/kg | Cr µg/kg | Al % | Fe % | Cr % |
| Initial H2O2 | 76 | 92 | 23 |  |  |  |
| extraction 1 | 3.8 | 0.9 | 6 | 95.0 | 99.0 | 73.9 |
| extraction 2 | 1.3 | 0.16 | 1.3 | 98.3 | 99.8 | 94.3 |
| extraction 3 | 0.7 | 0.05 | 0.5 | 99.1 | 99.9 | 97.8 |
| extraction 4 | 1.2 | 0.08 | 0.22 | 98.4 | 99.9 | 99.0 |
| extraction 5 | 0.7 | <0.05 | 0.13 | 99.1 | 100 | 99.4 |

These results show that:
The efficiency of the extracting process is higher at 50° C. than at ambient temperature
Metal concentrations below 1 ppb in the crude can be achieved after 3 extractions for Al, Fe and Cr
After 5 extractions, Fe can be removed completely from the hydrogen peroxide solution.

Example 7: Continuous Extraction Trial 2 continuous flows of a crude solution of hydrogen peroxide at 40% concentration identical to the one used in Examples 5 and 6 above and of an organic solution containing a mixture of solvents and a chelating agent were mixed together continuously in a heated glass reactor. The organic solution consisted of:
80% w/w of Solvess®150
10% w/w of TOP
10% w/w of DEHPA The mixture between aqueous and organic phases was then fed continuously in a separating glass column filled with a packing glass in order to separate both phases. That process was then repeated in a second set of identical material. A schematic diagram of the used apparatus (installation) is set out in FIG. 1 attached. The mixture of solvents was permanently recycled inside this installation following a closed circuit. The flows for each solutions were:
50 ml/h for the aqueous hydrogen peroxide solution
100 ml/h for the organic extraction solution The total amount of organic solution recycled in the system was 1250 ml and the installation was fully kept at 50° C.

Figure 2:
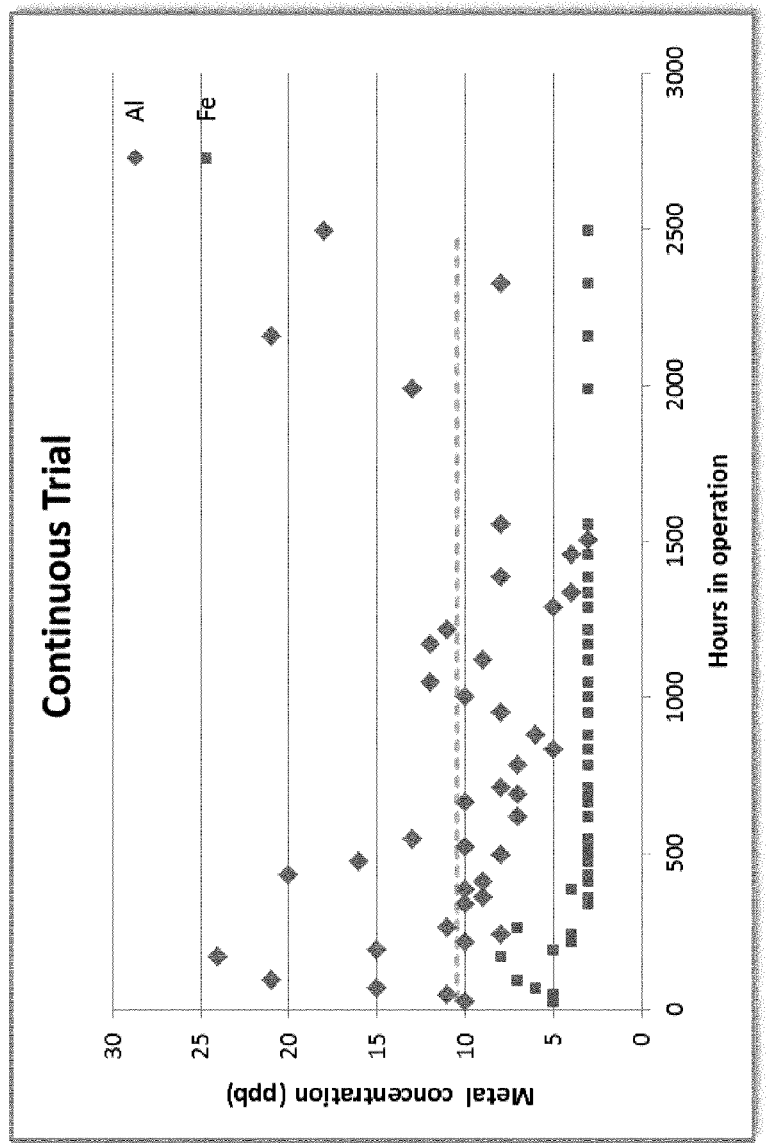
FIG. 2 shows the evolution of aluminium and iron content in the aqueous phase at the outlet of this installation.

Periodically a sample of the aqueous solution was taken at the outlet of the installation and analysed by ICP. The evolution of aluminium and iron content in the aqueous phase at the outlet of the installation is shown in FIG. 2 attached.

Figure 3:
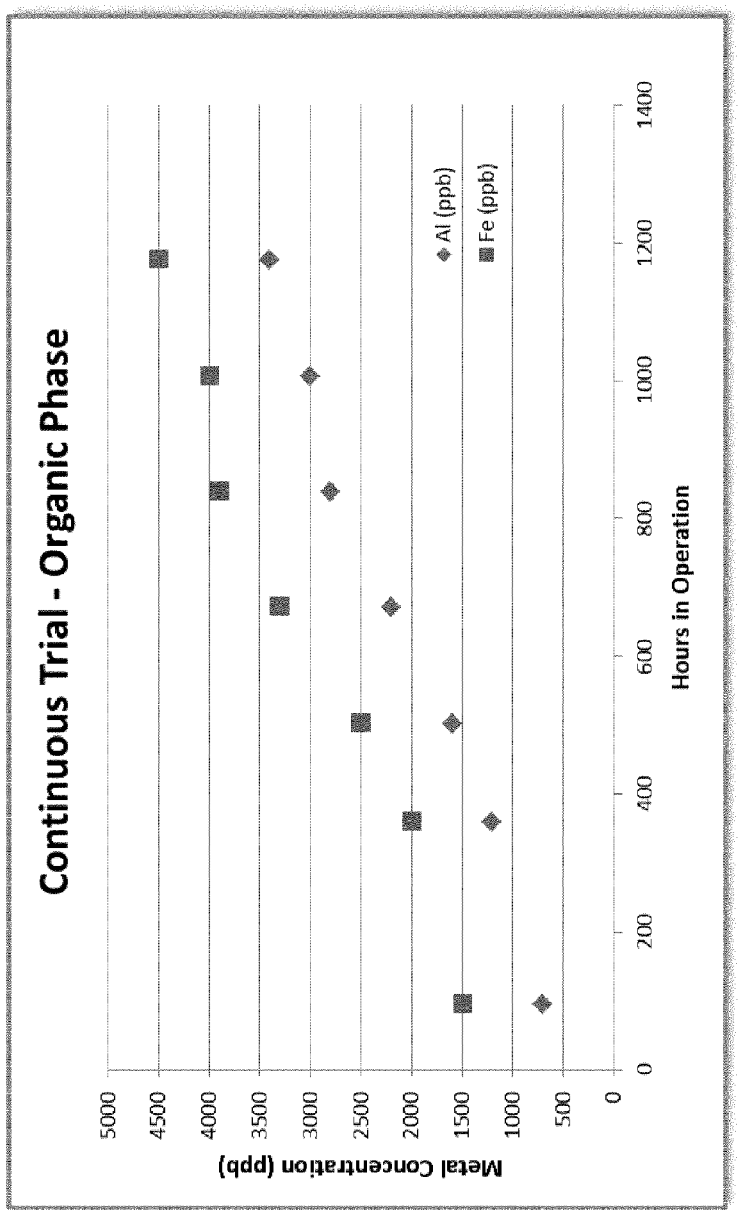
FIG. 3 shows the buildup of aluminium and iron in the organic phase inside said installation.
Figure 4:
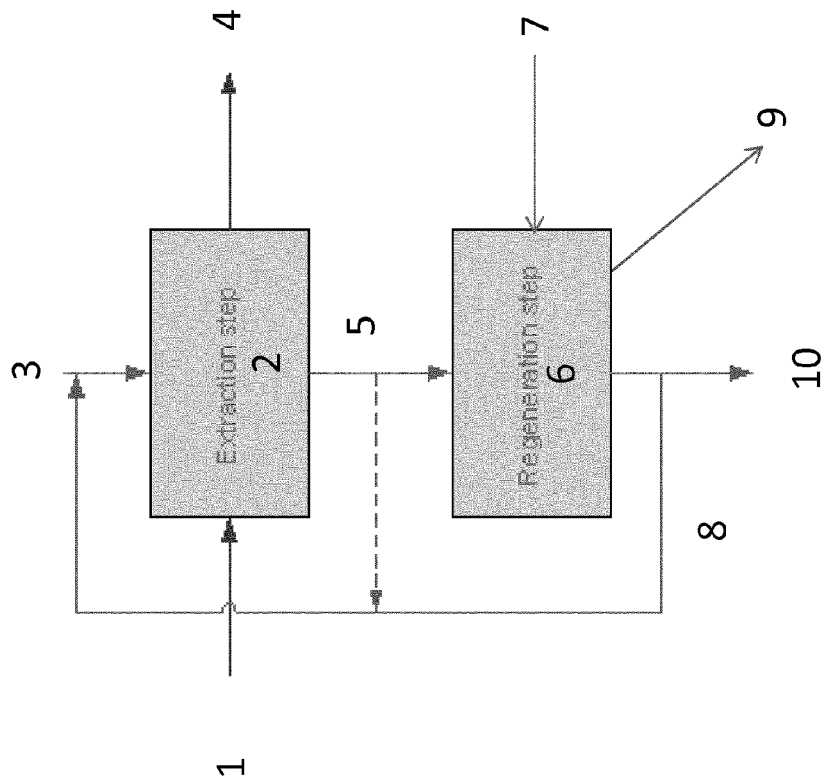

Periodically a sample of the organic solution was taken and analysed by ICP-MS. The buildup of aluminium and iron in the organic phase is shown in FIG. 3 attached.

These results show that:
An aluminium concentration in the outlet crude can be maintained below 20 ppb for almost 2500 hours of operation.
A concentration below 5 ppb of iron in the outlet hydrogen peroxide can be maintained on a long run.

1250 ml of extraction solution allowed purifying 125 l of hydrogen peroxide while maintaining a concentration of aluminium lower than 20 ppb in the crude.

Example 8: Regeneration of Exhausted Chelating Solution

The organic mixture of solvents and chelating agent used in the continuous extraction trial (example 7) has been used to test the regeneration procedure.

During the continuous trial, the inlet and outlet hydrogen peroxide solutions have been analysed periodically by ICP. By integration of these analytical results, the amount of aluminium in the organic solution at the end of the continuous test can be estimated to 10.2 mg/kg.

In a plastic fuel decanter, 100 ml of that organic extracting solution have been mixed for 30 minutes with 100 ml of $HNO_3$ 1 mol/l at ambient temperature and let to decant until a good separation is obtained between both phases.

Then the nitric acid solution was recovered and its aluminium content analysed by ICP. The result obtained was 9.2 mg/kg of aluminium in the nitric phase.

Taking into account the density of hydrogen peroxide, the yield of aluminium regeneration was about:

$$9.2*100/(10.2*1.15)=78\%$$

The invention claimed is:

1. A process for manufacturing a purified aqueous hydrogen peroxide solution, comprising:
    washing a crude aqueous hydrogen peroxide solution with a mixture of at least one organic solvent and an organophosphorus chelating agent,
    wherein the crude aqueous hydrogen peroxide solution is made by auto-oxidation of at least one alkylanthraquinone in a working solution comprising at least one organic solvent and the at least one alkylanthraquinone;
    wherein the organic solvent used for the washing step is not part of the working solution and is not recycled into it.

2. The process according to claim 1, wherein the at least one organic solvent used in the washing is chosen so that it improves the metal extraction by the organophosphorus chelating agent.

3. The process according to claim 2, wherein the at least one organic solvent comprises an organophosphorus compound different from the organophosphorus chelating agent.

4. The process according to claim 3, wherein the organophosphorus chelating agent is di-(2-ethylhexyl) phosphoric acid and the at least one organic solvent comprises trioctylphosphate or triethylhexylphosphate.

5. A process for manufacturing propylene oxide (1,2-epoxypropane) by reaction of propylene with hydrogen peroxide that comprises hydrogen peroxide washed by a process according to claim 1.

6. The process for manufacturing propylene oxide (1,2-epoxypropane) according to claim 5, wherein the washed hydrogen peroxide is in the form of an aqueous hydrogen peroxide solution containing from 1 to 100 ppb of Al and/or Fe.

7. The process according to claim 6, wherein the aqueous hydrogen peroxide solution contains less than 100 ppb of Cr.

8. The process according to claim 3, wherein the organic solvent used for the washing step comprises an organophosphorus compound chosen from alkyl-phosphates and alkyl-phosphonates.

9. The process of claim 5, wherein the hydrogen peroxide is in the form of an aqueous hydrogen peroxide solution that comprises less than 100 ppb of Al and/or Fe.

10. The process according to claim 5, wherein the hydrogen peroxide is in the form of an aqueous hydrogen peroxide solution that comprises less than 100 ppb of Cr.

11. The process of claim 6, wherein the aqueous hydrogen peroxide solution comprises from 10 to 100 ppb of Al and/or Fe.

12. The process according to claim 6, wherein the aqueous hydrogen peroxide solution contains from 1 to 100 ppb of Cr.

13. The process according to claim 6, wherein the aqueous hydrogen peroxide solution contains from 10 to 100 ppb of Cr.

14. The process according to claim 3, wherein the organophosphorus chelating agent is di-(2-ethylhexyl) phosphoric acid and the at least one organic solvent comprises trialkylphosphine oxides.

* * * * *